US009519107B2

(12) United States Patent
Zerfas et al.

(10) Patent No.: US 9,519,107 B2
(45) Date of Patent: Dec. 13, 2016

(54) METHODS AND APPARATUS RELATED TO A LAUNCH CONNECTOR PORTION OF A URETEROSCOPE LASER-ENERGY-DELIVERY DEVICE (71) Applicant: Boston Scientific Scimed, Inc., Maple Grove, MN (US)

(72) Inventors: Jeffrey W. Zerfas, Bloomington, IN (US); Paul Jortberg, Windham, NH (US); Richard P. Tumminelli, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/090,060

(22) Filed: Apr. 4, 2016

(65) Prior Publication Data

US 2016/0216449 A1 Jul. 28, 2016

Related U.S. Application Data (63) Continuation of application No. 14/518,292, filed on Oct. 20, 2014, now Pat. No. 9,329,350, which is a
(Continued)

(51) Int. Cl.
*G02B 6/36* (2006.01)
*G02B 6/26* (2006.01)
(Continued)

(52) U.S. Cl.
CPC ............ *G02B 6/262* (2013.01); *G02B 6/3813* (2013.01); *G02B 6/4296* (2013.01);
(Continued)

(58) Field of Classification Search
CPC .................... G02B 6/4296; G02B 23/2453
See application file for complete search history.

(56) References Cited

U.S. PATENT DOCUMENTS 4,183,619 A 1/1980 Makuch
4,575,181 A 3/1986 Ishikawa
(Continued)

OTHER PUBLICATIONS

International Search Report and Written Opinion for International Application No. PCT/US2008/087948, mailed Mar. 13, 2009, 12 pages.
(Continued)

*Primary Examiner* — Rhonda Peace
(74) *Attorney, Agent, or Firm* — Bookoff McAndrews, PLLC (57) ABSTRACT In one embodiment, an apparatus includes an optical fiber made of a silica-based material. A proximal end portion of the optical fiber has an outer-layer portion. The proximal end portion can be included in at least a portion of a launch connector configured to receive electromagnetic radiation. The apparatus also includes a component that has a bore therethrough and can be made of a doped silica material. The bore can have an inner-layer portion heat-fused to the outer-layer portion of the optical fiber. The component can also have an index of refraction lower than an index of refraction associated with the outer-layer portion of the optical fiber.

16 Claims, 6 Drawing Sheets

Related U.S. Application Data continuation of application No. 13/828,911, filed on Mar. 14, 2013, now Pat. No. 8,888,378, which is a continuation of application No. 12/340,350, filed on Dec. 19, 2008, now Pat. No. 8,419,293.

(60) Provisional application No. 61/051,720, filed on Dec. 21, 2007.

(51) Int. Cl.

| | | |
|---|---|---|
| *G02B 6/38* | (2006.01) | |
| *G02B 23/24* | (2006.01) | |
| *G02B 23/26* | (2006.01) | |
| *G02B 6/42* | (2006.01) | |
| *A61B 18/24* | (2006.01) | |
| *A61B 17/00* | (2006.01) | |
| *G02B 6/036* | (2006.01) | |
| *A61B 18/00* | (2006.01) | |
| *A61B 18/22* | (2006.01) | |

(52) U.S. Cl.
 CPC ......... *G02B 23/2423* (2013.01); *G02B 23/26* (2013.01); *A61B 18/24* (2013.01); *A61B 2017/00477* (2013.01); *A61B 2018/00494* (2013.01); *A61B 2018/00505* (2013.01); *A61B 2018/00982* (2013.01); *A61B 2018/2222* (2013.01); *G02B 6/036* (2013.01); *G02B 6/4203* (2013.01); *G02B 2006/4297* (2013.01)

(56) References Cited

U.S. PATENT DOCUMENTS

| | | | |
|---|---|---|---|
| 4,678,273 A | 7/1987 | Vilhelmsson | |
| 4,737,011 A | 4/1988 | Iri et al. | |
| 4,762,385 A | 8/1988 | Fuse | |
| 4,880,452 A | 11/1989 | Kanamori et al. | |
| 4,934,785 A | 6/1990 | Mathis et al. | |
| 4,961,624 A | 10/1990 | Savitsky et al. | |
| 4,964,688 A | 10/1990 | Caldwell et al. | |
| 5,058,984 A | 10/1991 | Bulman et al. | |
| 5,134,677 A | 7/1992 | Leung et al. | |
| 5,152,761 A | 10/1992 | Muller et al. | |
| 5,167,686 A | 12/1992 | Wong | |
| 5,179,610 A | 1/1993 | Milburn et al. | |
| 5,241,613 A | 8/1993 | Li et al. | |
| 5,291,570 A | 3/1994 | Filgas et al. | |
| 5,390,270 A | 2/1995 | Hanzawa et al. | |
| 5,408,558 A | 4/1995 | Fan | |
| 5,452,392 A * | 9/1995 | Baker | G02B 6/4296 385/84 |
| 5,619,602 A | 4/1997 | Sandstrom et al. | |
| 5,621,835 A | 4/1997 | Takahashi et al. | |
| 5,729,643 A | 3/1998 | Hmelar et al. | |
| 5,745,626 A | 4/1998 | Duck et al. | |
| 5,859,944 A | 1/1999 | Inoue et al. | |
| 5,946,437 A | 8/1999 | Uchida et al. | |
| 6,238,103 B1 | 5/2001 | Ezawa | |
| 6,282,349 B1 | 8/2001 | Griffin | |
| 6,347,178 B1 | 2/2002 | Edwards et al. | |
| 6,634,799 B2 | 10/2003 | Auld | |
| 6,687,436 B2 | 2/2004 | Griffin | |
| 6,883,975 B2 | 4/2005 | Clarkin et al. | |
| 6,948,862 B2 | 9/2005 | Brown | |
| 7,090,411 B2 | 8/2006 | Brown | |
| 7,204,645 B2 | 4/2007 | Brown | |
| 7,284,915 B2 | 10/2007 | Healy et al. | |
| 7,447,409 B2 | 11/2008 | Griffin | |
| 7,488,116 B2 | 2/2009 | Steve | |
| 7,524,318 B2 | 4/2009 | Young et al. | |
| 7,540,668 B2 | 6/2009 | Brown | |
| 7,585,118 B1 * | 9/2009 | Lumpkin | G02B 6/3825 385/53 |
| 8,419,293 B2 | 4/2013 | Zerfas et al. | |
| 8,888,378 B2 | 11/2014 | Zerfas et al. | |
| 9,329,350 B2 * | 5/2016 | Zerfas | G02B 6/4296 |
| 2002/0110332 A1 | 8/2002 | Clarkin et al. | |
| 2002/0118924 A1 | 8/2002 | Murata | |
| 2003/0016922 A1 | 1/2003 | DeMartino et al. | |
| 2003/0026551 A1 | 2/2003 | Tan | |
| 2005/0025418 A1 | 2/2005 | Brown | |
| 2005/0049459 A1 | 3/2005 | Hern | |
| 2005/0058410 A1 | 3/2005 | Healy et al. | |
| 2007/0122084 A1 | 5/2007 | Stephen | |
| 2007/0172174 A1 | 7/2007 | Scerbak et al. | |
| 2007/0179485 A1 | 8/2007 | Yeik et al. | |
| 2007/0292087 A1 | 12/2007 | Brown | |
| 2009/0180745 A1 | 7/2009 | Zerfas et al. | |
| 2009/0299352 A1 | 12/2009 | Zerfas et al. | |
| 2010/0198009 A1 | 8/2010 | Farr et al. | |
| 2015/0066004 A1 * | 3/2015 | Zerfas | G02B 6/4296 606/15 |

OTHER PUBLICATIONS

Optoskand Fiber Optic Cables, Sven-Olov Roos, Mar. 26, 2002, 12 pages.

* cited by examiner

METHODS AND APPARATUS RELATED TO A LAUNCH CONNECTOR PORTION OF A URETEROSCOPE LASER-ENERGY-DELIVERY DEVICE

RELATED APPLICATION

This application is a continuation of U.S. patent application Ser. No. 14/518,292, filed Oct. 20, 2014, which is a continuation of U.S. patent application Ser. No. 13/828,911, filed Mar. 14, 2013, now U.S. Pat. No. 8,888,378, which is a continuation of U.S. patent application Ser. No. 12/340,350, filed Dec. 19, 2008, now U.S. Pat. No. 8,419,293, which claims benefit to U.S. Provisional Patent Application No. 61/015,720, filed on Dec. 21, 2007, all of which are incorporated herein by reference in their entireties.

BACKGROUND

Embodiments relate generally to optical medical devices, and, in particular, to methods and apparatus related to a connector portion of a laser-energy-delivery device.

A variety of known endoscope types can be used during a medical procedure related to, for example, a ureteroscopy or colonscopy. Some of these known endoscope types include and/or can be used with a laser-energy-delivery device configured for treatment of a target area (e.g., a tumor, a lesion, a stricture). The laser-energy-delivery device can include an optical fiber through which laser energy is delivered to the target area from a laser energy source. Laser energy from the laser energy source can be emitted into a proximal end (also can be referred to an entry end) of the optical fiber and propagated along the optical fiber until the laser energy is delivered to the target area out of a distal end of the optical fiber.

Laser energy that is not completely delivered into the proximal end of the optical fiber (can be referred to as stray laser energy or leaked laser energy) can adversely affect the mechanical properties and/or optical properties of the laser-energy-delivery system. For example, the stray laser energy can result in inefficient delivery of laser energy and/or damage to the laser-energy-delivery system. In some cases, an optical fiber can be susceptible to burning and/or breaking during operation when stray laser energy enters into and weakens a coating around the optical fiber. The stray laser energy can enter into, for example, a cladding layer of the optical fiber and can overfill the cladding in an undesirable fashion (e.g., a damaging fashion) when the optical fiber is bent during operation. The stray laser energy can be caused by misalignment of an output focal spot of the laser energy source with the proximal end of the optical fiber because of, for example, improper maintenance of the laser energy source or focal spot drift.

Although known coupling components (e.g., tapered coupling components) have been designed to deal with stray laser energy, these known coupling components can lack stability, can increase the effective numerical aperture (NA) of guided light which can lead to premature failure of a laser fiber when bent, redirect laser energy inefficiently, are relatively expensive to manufacture, and/or require relatively large heat sinks. Thus, a need exists for a coupling component that can increase the longevity of a laser-energy-delivery system, increase laser energy transmission efficiency, and/or reduce heat sink requirements.

SUMMARY

In one embodiment, an apparatus includes an optical fiber made of a silica-based material. A proximal end portion of the optical fiber has an outer-layer portion. The proximal end portion can be included in at least a portion of a launch connector configured to receive electromagnetic radiation. The apparatus also includes a component that has a bore therethrough and can be made of a doped silica material. The bore can have an inner-layer portion heat-fused to the outer-layer portion of the optical fiber. The component can also have an index of refraction lower than an index of refraction associated with the outer-layer portion of the optical fiber.

DETAILED DESCRIPTION

A laser-energy-delivery device can be configured to receive laser energy emitted (also can be referred to as being launched) from a laser energy source. Specifically, the laser-energy-delivery device can receive the laser energy at a connector portion of the laser-energy-delivery device. The connector portion can be at a proximal end portion (can be referred to as an entry end portion) of the laser-energy-delivery device. In some embodiments, the connector portion can be referred to as a launch connector portion or as a launch connector because laser energy can be emitted into (e.g., launched into) the connector portion. The laser-energy-delivery device can also include an optical fiber coupled to the connector portion of the laser-energy-delivery device. Laser energy can be propagated within the optical fiber coupled to the connector portion until the laser energy is transmitted from the distal end of the optical fiber toward, for example, a target treatment area within a body of a patient. The connector portion can include a doped silica component that has an inner surface heat-fused to an outer portion of the optical fiber. All or substantially all of the surface area of the inner surface of the doped silica component can be heat-fused to the outer portion of the optical fiber. In some embodiments, the doped silica component can be referred to as a doped silica capillary or as a doped silica ferrule.

The optical fiber can be a silica-based optical fiber and can include, for example, a fiber core, one or more cladding layers (e.g., a cladding layer disposed around the fiber core), a buffer layer (e.g., a buffer layer disposed around a cladding layer), and/or a jacket (e.g., a jacket disposed around a buffer layer). In some embodiments, a numerical aperture of the fiber core with respect to one or more cladding layers around the fiber core can be between 0.1 and 0.3. In some embodiments, a numerical aperture of the cladding layer(s) with respect to the buffer layer can be between 0.2 and 0.6. At least a portion of the cladding layer(s), the buffer layer, and/or the jacket can be stripped from the optical fiber before the doped silica component is heat-fused to the optical fiber. At least a portion of the doped silica component (e.g., the inner surface of the doped silica component) can have an index of refraction lower than an index of refraction associated with the outer portion of the optical fiber. The doped silica component can be doped with a concentration of a dopant (e.g., a fluorine dopant, a chlorine dopant, a rare-earth dopant, an alkali metal dopant, an alkali metal oxide dopant, etc.) that can, at least in part, define the index of refraction of the doped silica component.

Because of the difference in the respective indices of refraction of the doped silica component and the outer portion of the optical fiber (e.g., cladding layer), laser energy (e.g., stray laser energy) from within the optical fiber and incident on an interface defined by the doped silica component and the outer portion of optical fiber is totally or substantially totally internally reflected within the optical fiber. In some embodiments, stray laser energy that is, for example, not totally or substantially totally internally reflected can be absorbed within the doped silica component.

A proximal end of the connector end portion of the laser-energy-delivery device can be defined so that it is flat and within a plane that is substantially normal to a longitudinal axis (or centerline) of the laser-energy-delivery device. In some embodiments, the doped silica component can be formed from, for example, a doped silica pre-form before being fused to an optical fiber. The connector portion of the laser-energy-delivery device can be coupled to (e.g., adhesively bonded to, press fit with) a component such as a metal ferrule, a housing, and/or a grip member. In some embodiments, the optical fiber can have a spherical distal end portion, a straight-firing distal end portion, or can have a side-firing distal end portion.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., a medical practitioner, a nurse, a technician, etc.) who would insert the medical device into the patient. Thus, for example, a laser energy deliver device end inserted inside a patient's body would be the distal end of the laser energy deliver device, while the laser energy deliver device end outside a patient's body would be the proximal end of the laser energy deliver device.

Figure 1:
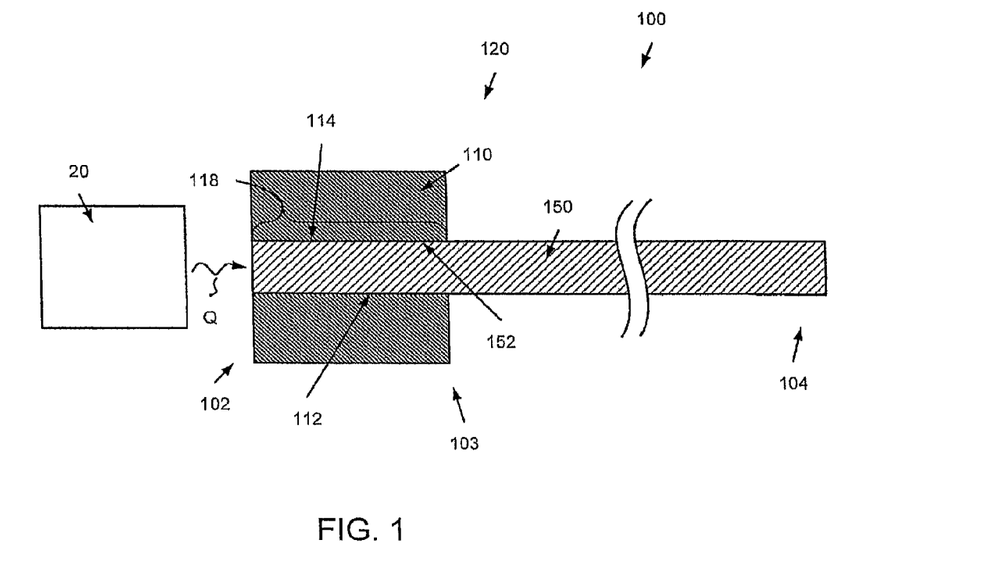
FIG. 1 is a schematic diagram of a side cross-sectional view of a connector portion of a laser-energy-delivery device, according to an embodiment.

FIG. 1 is a schematic diagram of a side cross-sectional view of a connector portion 120 of a laser-energy-delivery device 100, according to an embodiment. The laser-energy-delivery device 100 can be associated with (e.g., used in conjunction with) an endoscope (not shown). The connector portion 120 of the laser-energy-delivery device 100, which is at a proximal end portion 102 of the laser-energy-delivery device 100 (also a proximal end portion 102 of a doped silica component 110), is configured to receive laser energy Q emitted from a laser energy source 20. The laser energy source 20 can be, for example, a holumium (Ho) laser source, a holmium:YAG (Ho:YAG) laser source, a neodymium-doped:YAG (Nd:YAG) laser source, a semiconductor laser diode, and/or a potassium-titanyl phosphate crystal (KTP) laser source. In some embodiments, the numerical aperture of laser energy emitted from the laser energy source 20 can be between 0.1 and 0.4. The laser energy Q can be associated with a range of electromagnetic radiation from an electromagnetic radiation spectrum.

The laser energy Q emitted from the laser energy source 20 and received at the connector portion 120 of the laser-energy-delivery device 100 can be propagated along an optical fiber 150 until at least a portion of the laser energy Q is transmitted from a distal end portion 104 of the laser-energy-delivery device 100. In other words, the optical fiber 150 can function as a wave-guide for the laser energy Q.

The optical fiber 150 can be a silica-based optical fiber and can have, for example, a fiber core (not shown in FIG. 1). In some embodiments, the fiber core can be made of a suitable material for the transmission of laser energy Q from the laser energy source 20. In some embodiments, for example, the fiber core can be made of silica with a low hydroxyl (Om ion residual concentration. Laser energy wavelengths ranging from about 500 nm to about 2100 nm can be propagated within the fiber core during a surgical procedure. An example of low hydroxyl (low-OH) fibers used in medical devices is described in U.S. Pat. No. 7,169,140 to Kume, the disclosure of which is incorporated herein by reference in its entirety. The fiber core can be a multi-mode fiber core and can have a step or graded index profile. The fiber core can also be doped with a concentration of a dopant (e.g., an amplifying dopant).

The optical fiber 150 can also have one or more cladding layers (not shown in FIG. 1) and/or a buffer layer (not shown in FIG. 1) such as an acrylate layer. The fiber core and/or cladding layer(s) can be pure silica and/or doped with, for example, fluorine. The cladding can be, for example, a single or a double cladding that can be made of a hard polymer or silica. The buffer layer can be made of a hard polymer such as Tefzel®, for example. When the optical fiber 150 includes a jacket (not shown in FIG. 1), the jacket can be made of Tefzel®, for example, or can be made of other polymer-based substances.

Although not shown in FIG. 1, the laser energy source 20 can have a control module (not shown) configured to control (e.g., set, modify) a timing, a wavelength, and/or a power of the emitted laser energy Q. In some embodiments, the laser energy Q can have a power of between 1 watt and 10 kilowatts. In some embodiments, the control module can also be configured to perform various functions such as laser selection, filtering, temperature compensation, and/or Q-switching. The control module can be a hardware-based control module and/or a software-based control module that can include, for example, a processor and/or a memory.

The connector portion 120 has a doped silica component 110 fused to the optical fiber 150 at the proximal end portion 102 of the laser-energy-delivery device 100. As shown in FIG. 1, the optical fiber 150 is disposed within at least a portion of the doped silica component 110. In some embodiments, the doped silica component 110 can be referred to as a doped silica ferrule, a doped silica capillary, or a doped silica tube. More details related to the dimensions of the doped silica component 110 and the optical fiber 150 are described in connection with FIG. 2 and FIG. 3. In some embodiments, a metal ferrule (not shown in FIG. 1) or a housing (not shown in FIG. 1), for example, can be coupled to the doped silica component 110. More details related to components that can be coupled to the doped silica component 110 are described in connection with FIGS. 4 through 8B.

The doped silica component 110 is doped such that an index of refraction of at least an inner surface 114 of the doped silica component 110 is lower than or equal to an index of refraction of an outer surface 152 of the optical fiber 150. In some embodiments, the doped silica component 110 can be doped with a concentration of fluorine. In some embodiments, the doped silica component 110 can be uniformly doped or doped in a non-uniform (e.g., graded) fashion. Because of the difference in the indices of refraction, a portion of the laser energy Q propagated within the optical fiber 150 and incident on an interface 112 defined by the inner surface 114 of the doped silica component 110 and the outer surface 152 of the optical fiber 150 can be totally or substantially totally internally reflected within the optical fiber 150. If the optical fiber 150 has a cladding layer (not shown), a portion of the laser energy Q propagated within the cladding layer and incident on the interface 112 can be totally or substantially totally internally reflected within the cladding layer. If the index of refraction of the doped silica component 110 were, for example, substantially equal to that of the outer surface 152 of the optical fiber 150, an undesirable (e.g., a damaging) percentage of the laser energy Q could be transmitted into the doped silica component 110 and into, for example, surrounding components.

In some embodiments, the interface 112 can be configured to redirect a portion of the laser energy Q (e.g., stray laser energy) emitted near the interface 112 because of for example, misalignment of the laser energy source 20 with the connector portion 120. In some embodiments, a portion of the laser energy Q emitted directly into the doped silica component 110 can be at least partially absorbed within the doped silica component 110. Misalignment can be caused by improper alignment of the laser energy source 20 with the connector portion 120. Misalignment can also be caused by drift in targeting of emitted laser energy Q by the laser energy source 20 and/or thermo-lensing effects associated with the laser energy source 20.

During manufacture, at least a portion of the doped silica component 110 is heat-fused to the optical fiber 150. Specifically, at least a portion of the doped silica component 110 and the optical fiber 150 are heated so that the inner surface 114 of the doped silica component 110 is fused to the outer surface 152 of the optical fiber 150. In some embodiments, multiple areas (e.g., longitudinally discontinuous) along a length 118 of the doped silica component 110 can be heat-fused to the optical fiber 150. The areas may or may not continuously surround (e.g., circumferentially surround) the optical fiber 150. For example, a portion of the doped silica component 110 near or at the proximal end portion 102 of the doped silica component 110 and/or a portion of the doped silica component 110 near or at a distal end 103 of the doped silica component 110 can be heat-fused to the optical fiber 150. In some embodiments, a top surface area portion and/or a bottom surface area portion of the optical fiber 150 can be heat-fused to the inner surface 114 of the doped silica component 110 without heat-fusing the remaining portions (e.g., the bottom surface area portion of the top surface area portion, respectively). More details related to a method for heat-fusing the doped silica component 110 to the optical fiber 150 are described in connection with FIG. 3.

In some embodiments, the doped silica component 110 can be made separately from the optical fiber 150 and shaped so that the optical fiber 150 can be inserted into the doped silica component 110. For example, in some embodiments, the doped silica component 110 can have a cylindrical shape and a circular bore (e.g., a lumen) within which the optical fiber 150 can be inserted.

In some embodiments, the laser-energy-delivery device 100 can be used within an endoscope (not shown) that can define one or more lumens (sometimes referred to as working channels). In some embodiments, the endoscope can include a single lumen that can receive therethrough various components such as the laser-energy-delivery device 100. The endoscope can have a proximal end configured to receive the distal end portion 104 of the laser-energy-delivery device 100 and a distal end configured to be inserted into a patient's body for positioning the distal end portion 104 of the laser-energy-delivery device 100 in an appropriate location for a laser-based surgical procedure. The endoscope can include an elongate portion that can be sufficiently flexible to allow the elongate portion to be maneuvered within the body. In some embodiments, the endoscope can be configured for use in a ureteroscopy procedure.

The endoscope can also be configured to receive various medical devices or tools through one or more lumens of the endoscope, such as, for example, irrigation and/or suction devices, forceps, drills, snares, needles, etc. An example of such an endoscope with multiple lumens is described in U.S. Pat. No. 6,296,608 to Daniels et al., the disclosure of which is incorporated herein by reference in its entirety. In some embodiments, a fluid channel (not shown) is defined by the endoscope and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscope, for example, and coupled to a proximal end portion of an optical fiber that can be disposed within a lumen of the endoscope. Such an embodiment allows a medical practitioner to view the interior of a patient's body through the eyepiece.

Figure 2A:
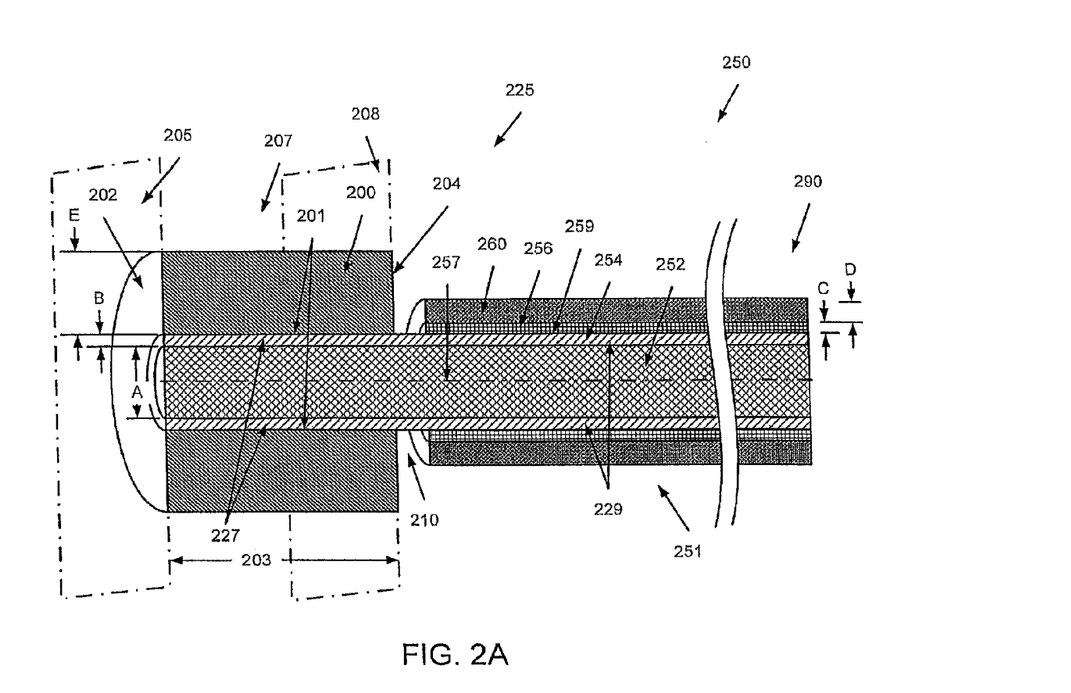
FIG. 2A is a schematic diagram of a side cross-sectional view of a connector portion of a laser-energy-delivery device, according to an embodiment.

FIG. 2A is a schematic diagram of a side cross-sectional view of a connector portion 225 of a laser-energy-delivery device 250, according to an embodiment. The laser-energy-delivery device 250 includes an optical fiber 251. As shown in FIG. 2A, a doped silica capillary 200 is heat-fused to a first portion 227 of a cladding layer 254 of the optical fiber 251. The first portion 227 is at a proximal end portion 207 of the optical fiber 251. The cladding layer 254 is disposed around a fiber core 252 of the optical fiber 251. A coating 256 is disposed around a second portion 229 of the cladding layer 254 of the optical fiber 251 and a jacket 260 is disposed around the coating 256. In some embodiments, the coating 256 can be, for example, an acrylate coating such as a fluorinated acrylate coating. The coating 256 can also be referred to as a buffer layer. In some embodiments, the jacket 260 can be made of a polymer-based material such as an ethylene tetrafluoroethylene (ETFE) copolymer and/or a nylon-based material. The second portion 229 of the cladding layer 254 is distal to the first portion 227 of the cladding layer 254. In some embodiments, the optical fiber 251 can have multiple cladding layers (not shown).

Laser energy (not shown) emitted into the connector portion 225 of the laser-energy-delivery device 250 can be propagated along the optical fiber 251 and transmitted out of a distal end 290 of the optical fiber 251. Although the portions (e.g., cladding layer 254) included within the laser-energy-delivery device 250 can have a variety of cross-sectional shapes such as ovals, and so forth, the portions are shown and described as circular-shaped portions.

In some embodiments, the doped silica capillary 200 can have a length 203 of, for example, 1 centimeter (cm) to 8 cm. In some embodiments, the length 203 of the doped silica capillary 200 can be less than 1 cm. In some embodiments, the length 203 of the doped silica capillary 200 can be greater than 8 cm. In this embodiment, the entire length 203 of an inner surface 201 of the doped silica capillary 200 is heat-fused to the cladding layer 254 of the optical fiber 251. In some embodiments, the heat-fused Portion (e.g., the heat-fused area) can be less than the entire length 203 of the doped silica capillary 200. In some embodiments, the length of the heat-fused portion can vary depending on the length 203 of the doped silica capillary 200. For example, if the doped silica capillary 200 is greater than 3 cm, less than the entire length 203 of the doped silica capillary 200 can be heat-fused to the cladding layer 254.

The fiber core 252 of the optical fiber 251 can have an outer diameter A, for example, between approximately 20 micrometers (μm) to 1200 μm. The cladding layer 254 of the optical fiber 251 can have a thickness B, for example, between approximately 5 μm to 120 μm. In some embodiments, the outer diameter (not shown) of the cladding layer 254 can be 1 to 1.3 times the outer diameter A of the fiber core 252 of the optical fiber 251.

The coating 256 of the optical fiber 251 can have a thickness C, for example, between approximately 5 μm to 60 μm. The thickness of the coating 256 of the optical fiber 251 can be defined to increase the mechanical strength of the optical fiber 251 during flexing of the optical fiber 251. The jacket 260 of the optical fiber 251 can have a thickness D, for example, between approximately 5 μm to 500 μm. The doped silica capillary 200 can have a thickness E, for example, between 20 μm and several millimeters (mm).

The doped silica capillary 200 can be cut from a doped silica pre-form and heat-fused to the first portion 227 of the cladding layer 254 after portions of the coating 256 and the jacket 260 are stripped from the first portion 227 of the cladding layer 254. A relatively strong bond that is resistant to tensile forces (e.g., forces in the direction of a longitudinal axis 257 (or centerline) of the optical fiber 251) can be formed between the doped silica capillary 200 and the cladding layer 254 when they are heat-fused together. The doped silica capillary 200 and the cladding layer 254 can be heat-fused so that structural failure (e.g., separation) caused, for example, by shearing strain at specified tensile force levels can be substantially avoided. In other words, the heat-fused area can be sufficiently large to provide mechanical stability (e.g., resistance to shear forces) between the cladding layer 254 and the doped silica capillary 200. For example, the cladding layer 254 with a diameter of approximately 150 μm can be heat-fused with the doped silica capillary 200 so that the cladding layer 254 will not separate from the doped silica capillary 200 when up to approximately 3 pounds of force (e.g., tensile force) is applied between the doped silica capillary 200 and the cladding layer 254.

In this embodiment, an index of refraction of the doped silica capillary 200 is lower than an index of refraction of the cladding layer 254. Also, the index of refraction of the cladding layer 254 is lower than an index of refraction of the fiber core 252. The coating 256 has an index of refraction that is lower than the index of refraction of the cladding layer 254. In some embodiments, the coating 256 can have an index of refraction that is higher, lower, or substantially the same as the index of refraction of the doped silica capillary 200.

As shown in FIG. 2A, a proximal end 202 of the connector portion 225 of the laser-energy-delivery device 250 is within a single plane 205. The plane 205 is substantially normal to the longitudinal axis 257 (or centerline) of the optical fiber 251. In other words, the proximal end 202 of the connector portion 225 of the laser-energy-delivery device 250 is flat or substantially flat. After the doped silica capillary 200 is heat-fused to the cladding layer 254, the proximal end 202 of the connector portion 225 of the laser-energy-delivery device 250 can be modified (e.g., mechanically polished, modified using laser energy) until it is flat or substantially flat.

Although not shown, in some embodiments, the proximal end 202 of the connector portion 225 of the laser-energy-delivery device 250 can have a lens. For example, a lens can be coupled (e.g., bonded, fused) to the proximal end 202. In some embodiments, a lens can be formed from the doped silica capillary 200, cladding layer 254, and/or, fiber core 252 of the optical fiber 251.

Although not shown, in some embodiments, the proximal end 202 of the connector portion 225 is not flat. In some embodiments, for example, the cladding layer 254 and/or the fiber core 252 can be configured to protrude proximal to a proximal end of the doped silica capillary 200. In other words, a proximal portion of the cladding layer 254 and/or a proximal portion of the fiber core 252 can protrude proximal to the proximal end 202 of the connector portion 225, which is within plane 205. In some embodiments, a proximal end of the doped silica capillary 200 is configured to protrude proximally over a proximal end of the cladding layer 254 and/or a proximal end of the fiber core 252. In other words, the proximal end of the doped silica capillary 200, the proximal end of the cladding layer 254, and/or the proximal end of the fiber core 252 can be within different planes. In some embodiments, the different planes can be non-parallel.

As shown in FIG. 2A, an air gap 210 is disposed between the doped silica capillary 200 and portions of the layers (e.g., the coating 256) disposed around the cladding layer 254. Specifically the air gap 210 is disposed between the doped silica capillary 200 and the coating 256 as well as the jacket 260. In some embodiments, the coating 256 and/or the jacket 260 may be coupled to (e.g., in contact with, bonded to, fused to) the doped silica capillary 200.

As shown in FIG. 2A, a distal end 204 of the doped silica capillary 200 can be substantially flat and within a plane 208 parallel to plane 205. Although not shown, in some embodiments, the distal end 204 of the doped silica capillary 200 can have one or more surfaces non-parallel to plane 208. For example, at least a portion of the distal end 204 can have a concave portion and/or a convex portion. An example of a doped silica capillary 200 having a concave portion is described in connection with FIG. 4.

In some embodiments, the doped silica capillary 200 can be a monolithically formed component. In some embodiments, the doped silica capillary 200 can include multiple separate portions (e.g., discrete or discontinuous sections) that are individually or collectively fused to define the doped silica capillary 200. For example, the doped silica capillary 200 can include tubular sections that are serially disposed over the cladding layer 254. The tubular sections can be fused to one another as well as the cladding layer 254 of the optical fiber 251.

In some embodiments, a numerical aperture of laser energy guided within a portion of the optical fiber 251 proximal to plane 208 is substantially equal to a numerical aperture of laser energy guided within a portion of the optical fiber 251 disposed distal to plane 208. In some embodiments, the numerical aperture associated with a proximal end of the optical fiber 251 can be substantially unchanged along the fiber core 252 (and/or the cladding layer 254) disposed within the doped silica component 200. In some embodiments, the numerical aperture of the fiber core 252 along substantially the entire length of the optical fiber 251 is substantially constant. Thus, the optical fiber 251 can have a smaller bend diameter with substantially less laser energy leaked into, for example, the cladding layer 254 than if the numerical aperture of the optical fiber 251 were to increase along, for example, the doped silica component 200 (from the proximal end toward the distal end).

Figure 2B:
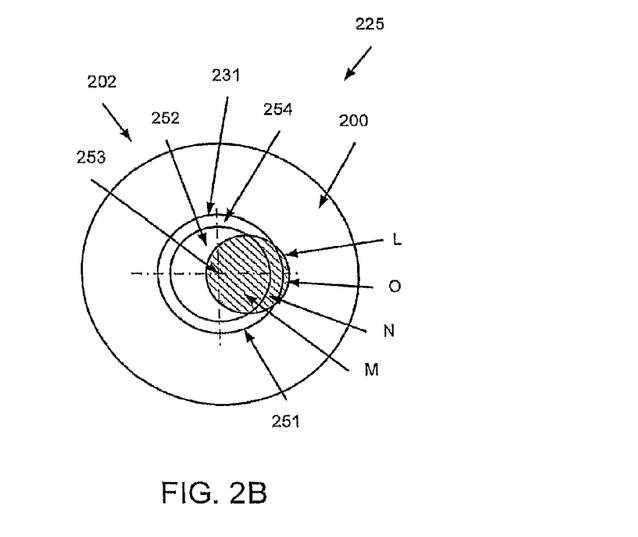
FIG. 2B is a schematic diagram of the proximal end of the connector portion shown in FIG. 2A, according to an embodiment.

FIG. 2B is a schematic diagram of the proximal end 202 of the connector portion 225 shown in FIG. 2A, according to an embodiment. As shown in FIG. 2B, a cross-sectional area L of laser energy emitted into the connector portion 225 is offset from a center 253 of the fiber core 252 of the optical fiber 251. The cross-sectional area L of the laser energy can be referred to as a laser spot or as a focal point spot. A portion M of the cross-sectional area L of the laser energy is emitted into the fiber core 252, a portion N of the cross-sectional area L of the laser energy is emitted into the cladding layer 254, and a portion O of the cross-sectional area L of the laser energy is emitted into the doped silica capillary 200. In some embodiments, the laser spot can have a diameter between 20 microns and 500 microns.

As shown in FIG. 2B, the doped silica capillary 200 and cladding layer 254 define an interface 231. Because the index of refraction of the doped silica capillary 200 is lower than the index of refraction of the cladding layer 254, the interface 231 totally or substantially totally internally reflects laser energy from within the cladding layer 254 and incident on the interface 231. Thus, the portion N of the laser energy that is emitted into the cladding layer 254 and incident on the interface 231 is totally or substantially totally internally reflected into the cladding layer 254 rather than transmitted into the doped silica capillary 200. The index of refraction of the doped silica capillary 200 and the index of refraction of the cladding layer 254 can be defined so that the interface 231 totally or substantially totally internally reflects incident laser energy at a desirable level.

The portion O of the cross-sectional area L of the laser energy that is directly emitted into the doped silica capillary 200 can be substantially absorbed or totally absorbed within the doped silica capillary 200 and/or dissipated in the form of heat. The doping concentration of the doped silica capillary 200 can be defined so that laser energy, such as laser energy, is absorbed and/or dissipated in the form of heat within the doped silica capillary 200 at a desirable rate.

Referring back to FIG. 2A, in some embodiments, at least a portion of laser energy can be emitted into the cladding layer 254 of the connector 225, for example, due to slight misalignment or spatial drift of the laser related to the laser-energy-delivery device 250. The cladding layer 254 can be used, along with the fiber core 252, as a transmission medium of the laser energy at least over the length 203 of the doped silica capillary 200. In some embodiments, laser energy emitted into the cladding layer 254 of the connector 225 can be initially guided by the interface 231 (shown in FIG. 2B) between the cladding layer 254 and the doped silica capillary 200. In some embodiments, the laser energy launched into the cladding layer 254 of the connector 225 can be reflected (e.g., guided) into the fiber core 252 by the interface 231 between the cladding layer 254 and the doped silica capillary 200 over the length 203 of the doped silica capillary 200. In other words, laser energy launched into the cladding layer 254 of the connector can migrate into the fiber core 252, for example, over the length 203 of the doped silica capillary 200. Thus, undesirable effects associated with overfill of laser energy within the cladding layer 254 during operation can be substantially reduced or avoided. When laser energy is emitted into the cladding layer 254 as well as the fiber core 252, the cladding layer 254 and fiber core 252 effectively collectively function as a fiber core, and the doped silica capillary 200 effectively functions as a cladding layer. If necessary, residual laser energy that is not reflected into the fiber core 252 by the interface 231 between the cladding layer 254 and the doped silica capillary 200 (within length 203) can be guided by an interface 259 between the cladding layer 254 and the coating 256.

As shown in FIG. 2A, the fiber core 252 (and cladding layer 254) of the connector portion 225 is substantially straight (not tapered). Even though the fiber core 252 of the connector portion 225 is substantially straight, the connector portion 225 can capture and guide more laser energy in the fiber core 252 and/or the cladding layer 254 than a fiber core connector portion with a tapered fiber core (not shown) for a given fiber core size and for a given laser spot size/numerical aperture. One reason this can be achieved is because of the laser energy reflective properties provided by the interface 231 between the cladding layer 254 and the doped silica capillary 200 of the connector portion 225. The substantially straight fiber core 252 (and cladding layer 254) of the connector portion 225 may not modify the effective numerical aperture of laser energy emitted into the fiber core 252 (and/or cladding layer 254) in an undesirable fashion. Thus, laser energy can be substantially guided within the fiber core 252 (and/or cladding layer 254) without penetrating the cladding layer 254 (if the effective numerical aperture of the laser energy were increased by, for example, tapering). In addition, undesirable overfill of the cladding layer 254 caused by bending of the fiber core 252 (which reduces the effective cone angle of laser energy relative to the cladding-coating interface 259) of the laser-energy-delivery device 250 during operation can be substantially reduced or avoided. This can be substantially reduced or avoided because the effective cone angle of laser energy relative to the cladding-coating interface 259 may not exceed the angle of total internal reflection.

Figure 3:
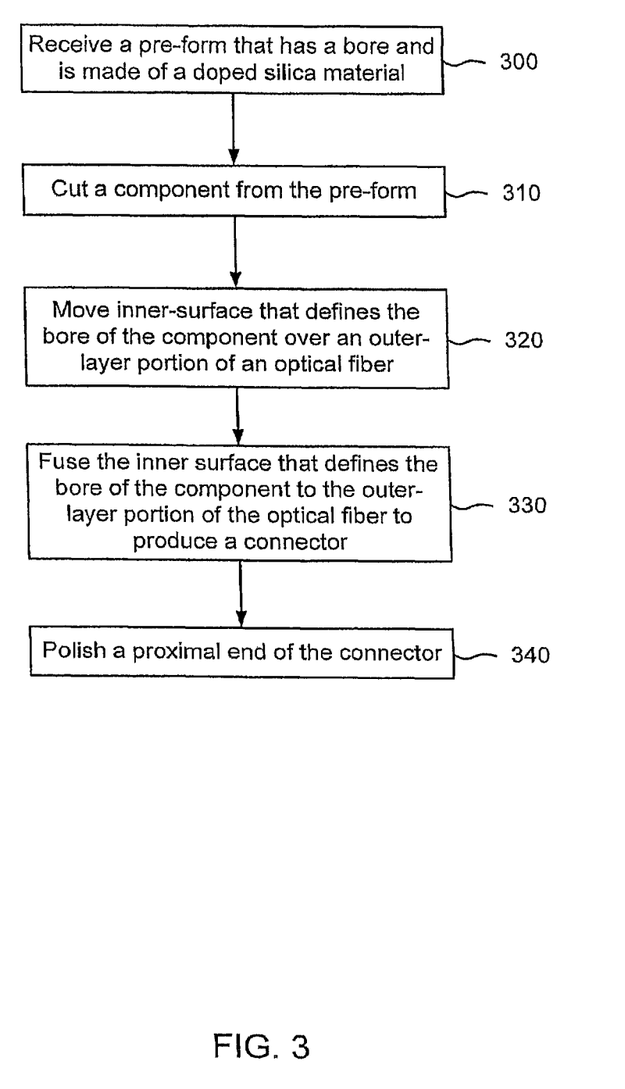
FIG. 3 is a flow chart that illustrates a method for producing a connector portion of a laser-energy-delivery device, according to an embodiment.

FIG. 3 is a flow chart that illustrates a method for producing a connector portion of a laser-energy-delivery device, according to an embodiment. As shown in FIG. 3, a pre-form that has a bore and is made of a doped silica material is received at 300. The pre-form can be a cylindrical (e.g., tube-shaped) pre-form that has a substantially uniform doping concentration. In some embodiments, the pre-form can have a non-uniform doping concentration. For example, the pre-form can have a doping concentration that is higher near an inner-surface that defines the bore than at an outer surface of the pre-form, and vice versa. In some embodiments, the pre-form can have a fluorine doping.

A component is cut from the pre-form at 310. The component can be cut from the pre-form using, for example, a laser energy cutting instrument or a mechanical cutting instrument. The component can be cut along a plane that is substantially normal to a longitudinal axis (or centerline) of the bore so that the bore is through the entire component. The length of the component can be, for example, a few centimeters.

An inner-surface that defines the bore of the component can be moved over an outer-layer portion of an optical fiber at 320. Specifically, a distal end of the inner-surface that defines the bore of the component can be moved in a distal direction over a proximal end of the outer-layer portion of the optical fiber. If the size of the bore of the component is defined such that it cannot be moved over the outer-layer portion of the optical fiber (e.g., an inner-diameter of a surface that defines the bore is smaller than an outer diameter of the outer-layer portion of the optical fiber), the size of the bore can be increased using, for example, a reaming process. In some embodiments, the inner diameter of the surface that defines the bore can be defined so that it is slight larger (e.g., several micrometers larger) than an outer diameter of the outer-layer portion of the optical fiber.

The outer-layer portion of the optical fiber can be associated with, for example, a cladding layer of the optical fiber. The cladding layer can be exposed after a coating and/or a jacket is removed (e.g., stripped) from the cladding layer. In some embodiments, the outer-layer portion of the optical fiber can be associated with a fiber core of the optical fiber. One more cladding layers can be removed to expose the fiber core of the optical fiber.

The inner-surface that defines the bore of the component can be moved over the outer-layer portion of the optical fiber until the distal end is within a specified distance of (e.g., within a micrometer, in contact with) an unstripped (e.g., remaining) portion of a jacket, a coating and/or a cladding layer(s) disposed around a portion of the optical fiber. In some embodiments, the unstripped portion of the jacket, the coating, and/or the cladding layer can be a stop for the component. In some embodiments, a portion of the jacket, the coating, and/or the cladding layer(s) can be disposed within a portion of the bore of the component (e.g., a tapered portion) after the inner-surface that defines the bore of the component is moved over the outer-layer portion of the optical fiber. A tapered portion of a bore of a component is described in connection with FIGS. 4 and 5.

The inner surface that defines the bore of the component is fused to the outer-layer portion of the optical fiber to produce a connector at 330. The inner surface can be heat-fused to the outer-layer portion using a heat source such as an electrical heating element, a flame, or a laser energy source (e.g., a carbon dioxide laser energy source). The inner surface can be heat-fused to the outer-layer portion incrementally. The component can be heat-fused to the optical fiber by first heating, for example, a distal end of the component and a distal end of the optical fiber using a heat source until they are heat-fused. The heat source can be moved (e.g., slowly moved) in a proximal direction until the desired portion of the inner surface (e.g., entire inner surface) of the component is heat-fused to the optical fiber. In some embodiments, the component and the optical fiber can be rotated about a longitudinal axis (or centerline) of the optical fiber during the heat-fusing process, for example, to promote even heating and/or heat-fusing around the entire inner surface of the component.

A proximal end of the connector is polished at 340. The proximal end of the connector (where laser energy can be received) can be polished until the proximal end is substantially flat and substantially normal to a longitudinal axis (or centerline) of the optical fiber. In some embodiments, the connector can be polished to remove, for example, a portion of a proximal end of the optical fiber protruding from the component. In some embodiments, the polishing process can include first mechanically grinding the proximal end of the connector. In some embodiments, the connector can be polished using, for example, a heat source such as a laser energy source.

Figure 4:
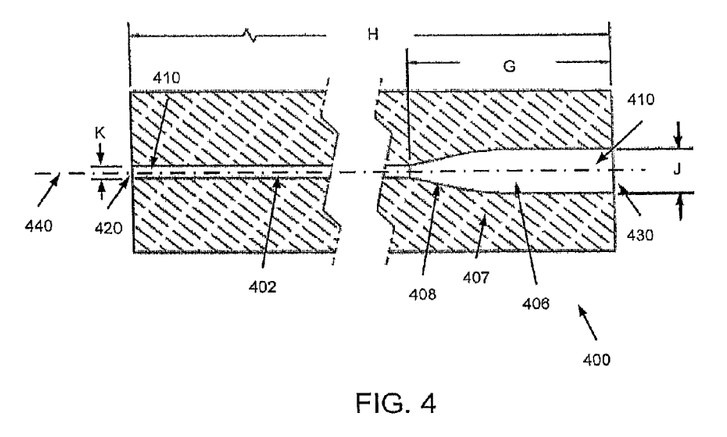
FIG. 4 is a schematic diagram that illustrates a side cross-sectional view of a doped silica capillary that has a receiving portion, according to an embodiment.

FIG. 4 is a schematic diagram that illustrates a side cross-sectional view of a doped silica capillary 400 that has a receiving portion 407, according to an embodiment. As shown in FIG. 4, the doped silica capillary 400 has a bore 410 through an entire length H of the doped silica capillary 400. In other words, the bore 410 is in fluid communication with an opening 420 at a proximal end of the doped silica capillary and an opening 430 at a distal end of the doped silica capillary 400. The bore 410 has a distal portion 406 that has a diameter J that is greater than a diameter K of a proximal portion 402 of the bore 410.

The bore has a tapered portion 408 disposed between the distal portion 406 of the bore 410 and the proximal portion 402 of the bore 410. The tapered portion 408 can taper along a longitudinal axis 440 (or centerline) of the doped silica capillary 400 as shown in FIG. 4. In this embodiment, the taper portion 408 increases in size in a distal direction along the bore 410. In some embodiments, the taper 408 can have flat portions (not shown).

The tapered portion 408 and the distal portion 406 of the bore 410 can collectively be referred to as the receiving portion 407. Although not shown, in some embodiments, a proximal end of an optical fiber (not shown) can be inserted into the receiving portion 407 of the bore 410 before the doped silica capillary 400 is heat-fused to the optical fiber. In some embodiments, a stripped portion of the optical fiber can be inserted into the distal portion 406 of the bore 410 at the receiving portion 407 and then into the remainder of the bore 410 (e.g., the proximal portion 402 of the bore 410). The diameter J of the bore 410 at the receiving portion 407 can have a size defined so that an unstripped portion of the optical fiber (e.g., an optical fiber with a jacket, a coating, and/or a cladding layer(s)) can fit into the bore 410 at the receiving portion 407. In some embodiments, the diameter J can be defined based on a diameter of a fiber core, a cladding layer, and/or a coating of an optical fiber configured to be heat-fused to the doped silica capillary 400. For example, the diameter J can be 5% to 100% larger than a diameter of a fiber core, a cladding layer, and/or a coating of an optical fiber.

The receiving portion 407 can have a length G that is approximately 1% to 20% of the entire length H of the doped silica capillary 400. In some embodiments, for example, the length G can be between 0.5 mm and 10 mm. In some embodiments, for example, the length H can be between 100 mm to 10 cm. In some embodiments, a doped silica capillary 400 can be defined with an abrupt change between two different sized (e.g., different diameter) lumen that define the bore 410. In other words, the doped silica capillary 400 can be defined without a tapered portion 408.

Figure 5:
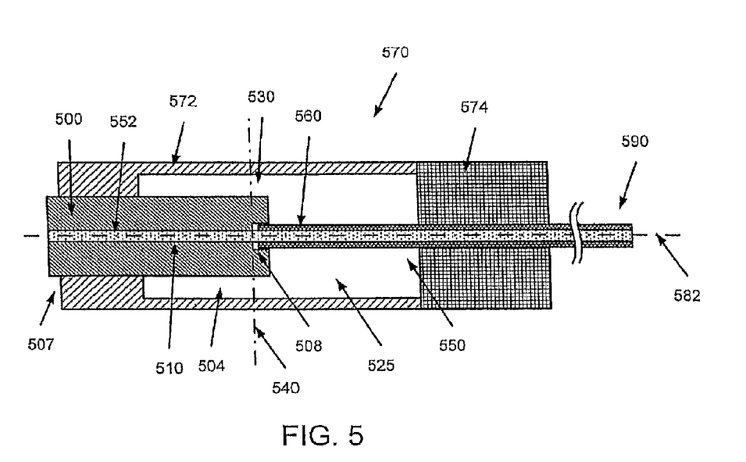
FIG. 5 is a schematic diagram that illustrates at least a portion of a laser-energy-delivery device disposed within a housing assembly, according to an embodiment.

FIG. 5 is a schematic diagram that illustrates at least a portion of a laser-energy-delivery device 550 disposed within a housing assembly 570, according to an embodiment. The laser-energy-delivery device 550 has a connector portion 507 at a proximal portion of the laser-energy-delivery device 550. The laser-energy-delivery device 550 has a portion of an optical fiber 552 (e.g., an optical fiber core and an optical fiber cladding layer(s)) disposed within a bore 510 of a doped silica capillary 500 of the connector portion 507. Distal to the doped silica capillary 500, the optical fiber 552 also has a coating 560. The coating 560 can include, for example, an acrylate coating, or an acrylate coating and a polymer-based jacket.

The housing assembly 570 has a capillary holder 572 coupled to the doped silica capillary 500 of the connector portion 507 of the laser-energy-delivery device 550. In some embodiments, the capillary holder 572 can be, for example, mechanically coupled to (e.g., friction fit with, press fit with, mechanically locked to) and/or adhesively coupled to the doped silica capillary 500.

As shown in FIG. 5, the capillary holder 572 is coupled to a proximal end portion of the doped silica capillary 500, but need not be coupled to a distal end portion 504 of the doped silica capillary 500. In some embodiments, the capillary holder 572 can be coupled to a portion of the doped silica capillary 500 that is distal to a receiving portion 508. In some embodiments, the capillary holder 572 can be coupled to a portion of the doped silica capillary 500 that is distal to a plane 540 that is substantially normal to a longitudinal axis 582 (or centerline) of the laser-energy-delivery device 550 and that is at a proximal end of the receiving portion 508. As shown in FIG. 5, the capillary holder 572 is coupled to the doped silica capillary 500 such that an air gap 525 is disposed between the capillary holder 572 and the distal end portion 504 of the doped silica capillary 500.

The housing assembly 570 also has an alignment assembly 574 coupled to the coating 560 of the optical fiber 552. In some embodiments, the alignment assembly 574 can be, for example, mechanically coupled to (e.g., friction fit with, press fit with, mechanically locked to) and/or adhesively coupled to the coating 560. The alignment assembly 574 can be configured hold the optical fiber 552 so that it substantially does not bend lateral to a longitudinal axis 582 (or centerline) of the optical fiber 552. For example, the alignment assembly 574 can be configured hold the optical fiber 552 so that it does not substantially bend in a direction substantially normal to a longitudinal axis 582 (or centerline) of the optical fiber 552. In some embodiments, the optical fiber 552 can hold the optical fiber 552 without plastically deforming, for example, the coating 560 or substantially altering the optical characteristics of the optical fiber 552.

The alignment assembly 574 can include, for example, a Sub-Miniature A (SMA) connector such as an SMA 905 connector. As shown in FIG. 5, the capillary holder 572 is coupled to the doped silica capillary 500 such that an air gap 525 is disposed between the alignment assembly 574 and the distal end portion 504 of the doped silica capillary 500. In some embodiments, the capillary holder 572 can be coupled to the alignment assembly 574. More details related to capillary holders and alignment assemblies are described in connection with FIGS. 6 through 8B.

As shown in FIG. 5, a portion of the coating 560 is at least partially disposed within the receiving portion 508 of the bore 510 of the doped silica capillary 500. In some embodiments, the portion of the coating 560 can be, for example, adhesively coupled to an inner surface of the receiving portion 508 of the bore 510.

Figure 6:
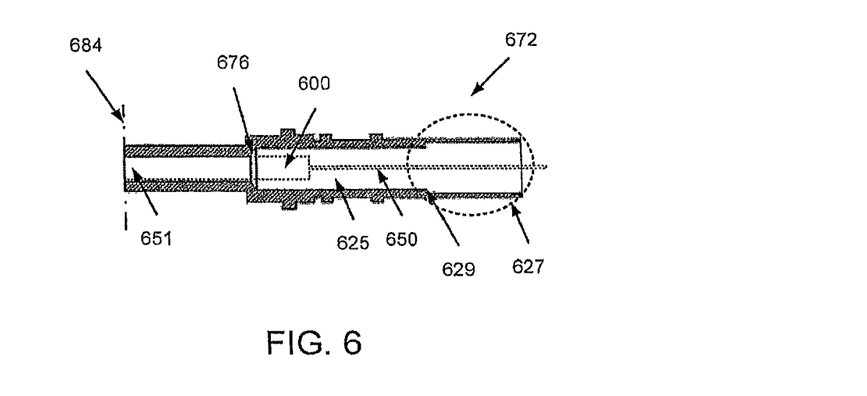
FIG. 6 is a schematic diagram of a side cross-sectional view of a capillary holder, according to an embodiment.

FIG. 6 is a schematic diagram of a side cross-sectional view of a capillary holder 672, according to an embodiment. A doped silica capillary 600 of a laser-energy-delivery device 650 (shown in dashed lines) is disposed within and coupled to the capillary holder 672. As shown in FIG. 6, a proximal end 651 of the laser-energy-delivery device 650 and a proximal end of the capillary holder 672 are within a plane 684. The capillary holder 672 has a taper portion 676 configured to facilitate ease of insertion of the proximal end 651 of the doped silica capillary 600 into the capillary holder 672 during assembly.

Figure 7:
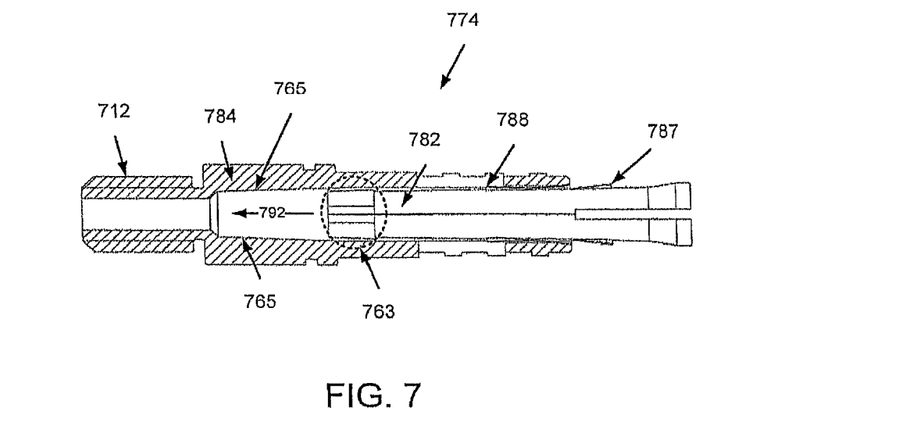
FIG. 7 is a schematic diagram of a side cross-sectional view of an alignment assembly, according to an embodiment.

The capillary holder 672 has a portion 627 configured to a receive a proximal end of an alignment assembly (not shown). FIG. 7 illustrates an example of an alignment assembly that can be inserted into the portion 627 of the capillary holder 672 shown in FIG. 6. Referring back to FIG. 6, the capillary holder 629 has a stop configured to prevent the alignment assembly from being inserted too far within the capillary holder 672. In some embodiments, the capillary holder 672 can be mechanically coupled to (e.g., press fit with, mechanically locked to, screw fit within) and/or adhesively coupled to the alignment assembly.

FIG. 7 is a schematic diagram of a side cross-sectional view of an alignment assembly 774, according to an embodiment. As shown in FIG. 7, the alignment assembly 774 includes a transition component 784 and an SMA connector component 782. The transition component 784 is configured to be coupled to (e.g., lockably coupled to) a capillary holder (not shown) such as that shown in FIG. 6. Specifically, a proximal end 712 of the transition component 784 shown in FIG. 7 can be disposed within a capillary holder when coupled to the capillary holder. In some embodiments, at least a portion of the transition component 784 can be configured to be disposed outside of a capillary holder when coupled to the capillary holder. The transition component 784 and SMA connector component 782 can be moved over a laser-energy-delivery device (not shown), for example, disposed within a capillary holder (not shown).

As shown in FIG. 7, the transition component 784 has a tapered inner wall 765 and the SMA connector component 782 has a slotted cylindrical press fit component 763. The slotted cylindrical press fit component 763 can also be referred to as a collet 763. As the collet 763 is moved in a proximal direction 792 within the transition component 784 and moved against the tapered inner wall 765 of the transition component 784, the collet 763 is configured to constrict around and hold a laser-energy-delivery device disposed within the SMA connector component 782. In some embodiments, a connector component (not shown) can be configured to be coupled to at least a portion of a laser-energy-delivery device using a different mechanism. For example, the connector component can be configured to clamp around the portion of the laser-energy-delivery device via a set screw, a constricting collar (that may be a separately manufactured component), and so forth. The connector component can also be coupled to the portion of the laser-energy-delivery device using, for example, an adhesive.

The SMA connector component 782 is configured to be mechanically coupled to the transition component 784 via a protrusion 787 that mechanically locks into a protrusion 788 of the transition component 784. As shown in FIG. 7, the SMA connector component 782 is partially disposed within, but not yet lockably coupled to the transition component 784. The SMA connector component 782 can be lockably coupled to the transition component 784 by moving the SMA connector component 782 in a proximal direction 792 within the transition component 784 until the protrusion 787 is disposed proximal to the protrustion 788 of the transition component 784.

Although the SMA connector component 782 is configured to be disposed inside of the transition component 784 (as shown in FIG. 7), in some embodiments, at least a portion of a connector component (not shown) can be configured to be disposed outside of (e.g., radially outside of) the transition component (not shown). In some embodiments, the connector component can be made of multiple pieces. In some embodiments, a connector component can be configured to be coupled to a transition component via a screw mechanism, an adhesive, multiple locking mechanisms, and so forth. In some embodiments, the connector component can have, for example, threads dispose on an outside portion of the connector component and the transition component can be configured to received the threads of the connector component. When the connector component is screwed into the transition component via the threads, the connector component can be configured to constrict around, for example, at least a portion of a laser-energy-delivery device.

Figure 8A:
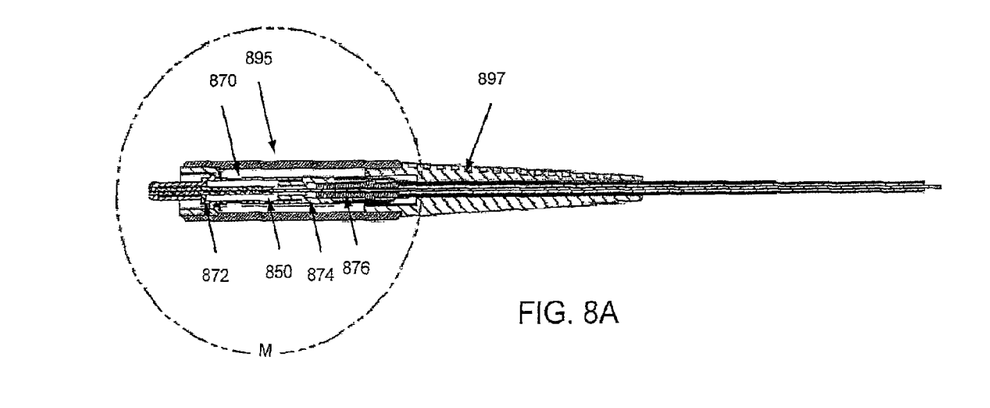
FIG. 8A is a schematic diagram of a side cross-sectional view of a grip assembly 895, according to an embodiment.

FIG. 8A is a schematic diagram of a side cross-sectional view of a grip assembly 895, according to an embodiment. A housing assembly 870 is disposed within the grip assembly 895, which is coupled to a boot 897. In some embodiments, for example, the boot 897 can be made of a rigid material (e.g., a rigid plastic material), and, in some embodiments, the boot 897 can be made of a flexible material (e.g., a flexible rubber material, a flexible plastic material). A laser-energy-delivery device 850 is coupled to a capillary holder 872, which is coupled to an alignment assembly that includes a transition component 874 at least partially disposed around an SMA connector component 876. An enlarged portion M of the grip assembly 895 is shown in FIG. 8B.

Figure 8B:
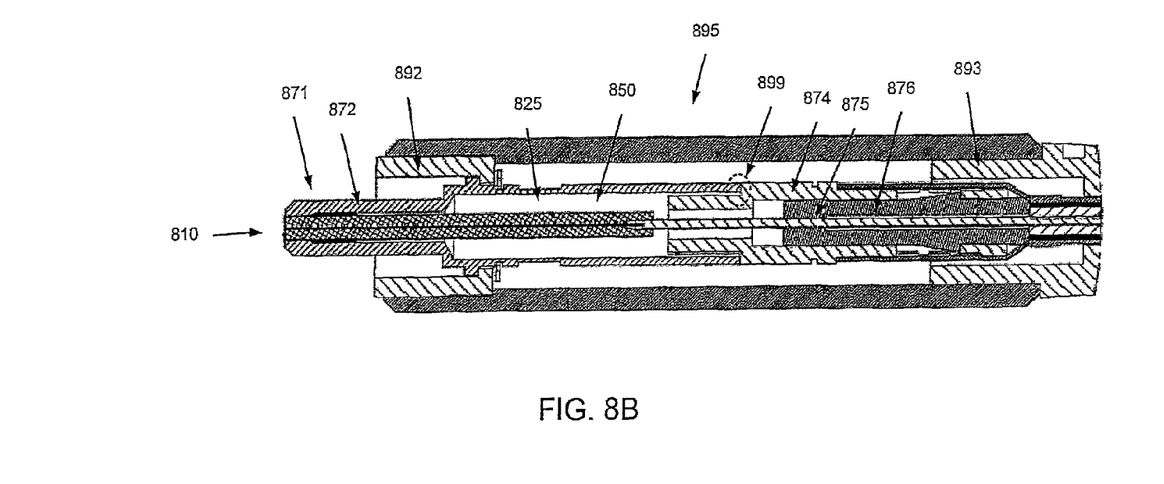
FIG. 8B is a schematic diagram of an enlarged view of the side cross-sectional view of the grip assembly shown in FIG. 8A, according to an embodiment.

FIG. 8B is a schematic diagram of an enlarged view of the side cross-sectional view of the grip assembly 895 shown in FIG. 8A, according to an embodiment. Laser energy from, for example, a laser energy source (not shown) can be received at a proximal end 810 of the laser-energy-delivery device 850. A proximal end portion 871 of the capillary holder 872 can be disposed within (e.g., proximate to) the laser energy source.

As shown in FIG. 8B, the capillary holder 872 is coupled to the grip assembly 895 via a first coupling nut 892 and a second coupling nut 893. The transition component 874 of the alignment assembly can be coupled to the capillary holder 872 at 899 via a locking mechanism (the locking mechanism is not shown). For example, a locking mechanism can include a protrusion from the capillary holder 872 that can be disposed within a cavity of the transition component 874. As shown in FIG. 8B, the SMA connector component 876 is holding the laser-energy-delivery device 850 at 875.

While various embodiments have been described above, it should be understood that they have been presented by way of example only, and not limitation. For example, the optical fiber components (e.g., connector end portion, laser-energy-delivery device, grip assembly) described herein can include various combinations and/or sub-combinations of the components and/or features of the different embodiments described. The optical fiber components, as well as the methods of using the optical fiber components, can be used in the treatment of various conditions in addition to those mentioned herein.

What is claimed is:

1. An apparatus, comprising:
    an optical fiber extending along a longitudinal axis and having a cladding layer and a silica core;
    a component made of a doped silica material defining a bore, a portion of the cladding layer of a proximal end portion of the optical fiber being in contact with the bore to define an interface, the optical fiber and the component collectively defining a launch connector;
    a holder having a proximal portion coupled to a proximal end portion of the launch connector;
    an alignment assembly extending distally of the holder and defining a lumen extending therethrough;
    a grip extending between a proximal end and a distal end of the grip, the grip being coupled to the launch connector; and
    a boot coupled to the grip, the boot extending distally of the distal end of the grip, wherein a proximal end of the boot has a first diameter and a distal end of the boot has a second diameter, different than the first diameter.

2. The apparatus of claim 1, wherein the proximal end portion of the launch connector is positioned proximally of the proximal end of the grip.

3. The apparatus of claim 2, wherein an inner circumferential wall of the grip adjacent the proximal end of the grip has a first diameter, and wherein the inner circumferential wall of the grip adjacent the distal end of the grip has a second diameter, different than the first diameter.

4. The apparatus of claim 1, wherein the second diameter of the boot is smaller than the first diameter of the boot.

5. The apparatus of claim 1, wherein the component includes a fluorine-doped silica material that has an index of refraction lower than an index of refraction of the cladding layer of the optical fiber.

6. The apparatus of claim 1, wherein the portion of the cladding layer is a first portion of the cladding layer and the bore is a first bore, wherein the optical fiber has a coating on a second portion of the cladding layer and not on the first portion of the cladding layer, the second portion of the cladding layer being disposed outside of the first bore of the component and disposed within a second bore of the component, and wherein the second bore of the component has an inner diameter greater than an inner diameter of the first bore of the component.

7. The apparatus of claim 1, wherein the holder defines a longitudinally extending air gap between the alignment assembly and a distal portion of the component.

8. An apparatus, comprising:
    an optical fiber extending along a longitudinal axis and having a cladding layer and a silica core;
    a component made of a doped silica material defining a bore, a portion of the cladding layer of the proximal end portion being in contact with the bore to define an interface, the optical fiber and the component collectively defining a launch connector;
    a holder having an open distal end and a proximal portion coupled to a proximal end portion of the launch connector;
    an alignment assembly extending distally of the holder and defining a lumen extending therethrough, a proximal end of the alignment assembly being positioned within the open distal end of the holder; and
    a distal coupling nut defining a cavity therein, wherein a distal end of alignment assembly is received within the cavity.

9. The apparatus of claim 8, wherein the proximal end of the alignment assembly has a first diameter and a distal end of the alignment assembly has a second diameter, larger than the first diameter.

10. The apparatus of claim 8, wherein the alignment assembly further includes a radially extending wall between the proximal end and the distal end of the alignment assembly, wherein the wall abuts the open distal end of the holder.

11. The apparatus of claim 8, further including a proximal coupling nut defining a cavity therein, wherein the proximal portion of the holder is received within the cavity of the proximal coupling nut.

12. The apparatus of claim 8, wherein the component includes a fluorine-doped silica material that has an index of refraction lower than an index of refraction of the cladding layer of the optical fiber.

13. An apparatus, comprising:
- a laser-energy-delivery device extending along a longitudinal axis and having an optical fiber, a cladding layer, and a doped silica capillary defining a bore, a portion of the cladding layer being in contact with the bore to define an interface;
- a holder having an open distal end and a proximal portion coupled to a proximal end portion of the laser-energy-delivery device;
- an alignment assembly extending distally of the holder and defining a lumen extending therethrough, a proximal end of the alignment assembly being positioned within the open distal end of the holder;
- a grip extending between a proximal end and a distal end of the grip, the grip being coupled to the laser-energy-delivery device; and
- a boot coupled to the grip, the boot extending distally of the distal end of the grip.

14. The apparatus of claim 13, wherein the capillary includes a fluorine-doped silica material that has an index of refraction lower than an index of refraction of the cladding layer.

15. The apparatus of claim 13, wherein the portion of the cladding layer is a first portion of the cladding layer and the bore is a first bore, wherein the optical fiber has a coating on a second portion of the cladding layer and not on the first portion of the cladding layer, the second portion of the cladding layer being disposed outside of the first bore of the capillary and disposed within a second bore of the capillary, and wherein the second bore of the capillary has an inner diameter greater than an inner diameter of the first bore of the capillary.

16. The apparatus of claim 13, wherein the holder defines a longitudinally extending air gap between the alignment assembly and a distal portion of the capillary.

* * * * *